(12) United States Patent
Thaning et al.

(10) Patent No.: US 9,272,056 B2
(45) Date of Patent: Mar. 1, 2016

(54) METHOD TO PRODUCE HYPERPOLARISED CARBOXYLATES

(75) Inventors: Mikkel Thaning, Tygelsjo (NO); Karl Andreas Gram, Oslo (NO)

(73) Assignee: GE Healthcare AS, Oslo (NO)

(*) Notice: Subject to any disclaimer, the term of this patent is extended or adjusted under 35 U.S.C. 154(b) by 1063 days.

(21) Appl. No.: 12/097,569

(22) PCT Filed: Dec. 15, 2006

(86) PCT No.: PCT/NO2006/000481
§ 371 (c)(1),
(2), (4) Date: Jun. 16, 2008

(87) PCT Pub. No.: WO2007/069909
PCT Pub. Date: Jun. 21, 2007

(65) Prior Publication Data
US 2008/0292551 A1    Nov. 27, 2008

(30) Foreign Application Priority Data
Dec. 16, 2005 (NO) .................................... 20055983

(51) Int. Cl.
*A61K 51/00* (2006.01)
*A61M 36/14* (2006.01)
*A61K 49/20* (2006.01)
*A61K 49/10* (2006.01)
*A61K 49/06* (2006.01)

(52) U.S. Cl.
CPC .............. *A61K 49/20* (2013.01); *A61K 49/10* (2013.01); *A61K 49/106* (2013.01); *A61K 49/06* (2013.01)

(58) Field of Classification Search
USPC ........................................................ 424/1.81
See application file for complete search history.

(56) References Cited

U.S. PATENT DOCUMENTS

| | | | | |
|---|---|---|---|---|
| 5,728,370 A | * | 3/1998 | Andersson et al. | 424/9.3 |
| 6,013,810 A | * | 1/2000 | Thaning | 549/31 |
| 2003/0194810 A1 | * | 10/2003 | Dotsch et al. | 436/18 |
| 2005/0233470 A1 | * | 10/2005 | Clark et al. | 436/173 |

FOREIGN PATENT DOCUMENTS

| | | |
|---|---|---|
| GB | 2252245 | 8/1992 |
| WO | 91/12024 | 8/1991 |
| WO | 96/39367 | 12/1996 |
| WO | 99/35508 | 7/1999 |
| WO | 03/089656 | 10/2003 |
| WO | 2005/024440 | 3/2005 |
| WO | 2006/011809 | 2/2006 |
| WO | 2006/011811 | 2/2006 |
| WO | 2007/064226 | 6/2007 |

OTHER PUBLICATIONS

Chou et al. (Biochem. 1980, 19, 1543-1549).*
Durst et al. (Clinc. Chem. 1972, 18, 206-208).*
WikipediaMeglumine 2013.*
PCT/NO2006/000481 Int'l Search Report/Written Opinion dated Aug. 2007.
Sorin, et.al. "Rejection of Gd(III) by nanofiltration assisted by complexation on charged organic membrane: Influences of pH, pressure, flux, strength and temperature" Journal of Membrane Science 267 (2005) pp. 41-49.
Donald, et.al. "Potential for decontamination of plutonium-containing solutions using transferring metalloprotein affinity metal chromatography" Journal of Inorganic Biochemistry, 56, 167-171 (1994) pp. 167-171.
Vigneau, et.al. "Ionic imprinted resins based on EDTA and DTPA derivatives for lanthanides (III) separation" Analytica Chimica Acta 435 (2001) pp. 75-82.

* cited by examiner

*Primary Examiner* — Michael G Hartley
*Assistant Examiner* — Melissa Perreira

(57) ABSTRACT

The invention relates to a dynamic nuclear polarisation method for producing hyperpolarised carboxylates of organic amines and amino compounds and compositions for use in that method. The DNP agent preferably is a stable oxygen-based, sulphur-based or carbon-based trityl radical. Optionally a paramagnetic metal ion is present.

19 Claims, No Drawings

METHOD TO PRODUCE HYPERPOLARISED CARBOXYLATES

This application is a filing under 35 U.S.C. 371 of international application number PCT/NO2006/000481, filed Dec. 15, 2006, which claims priority to application number 20055983 filed Dec. 16, 2005, in Norway the entire disclosure of which is hereby incorporated by reference.

The invention relates to a dynamic nuclear polarisation method for producing hyperpolarised carboxylates of organic amines and amino compounds and compositions for use in that method.

Magnetic resonance (MR) imaging (MRI) is an imaging technique that has become particularly attractive to physicians as it allows for obtaining images of a patient's body or parts thereof in a non-invasive way and without exposing the patient and the medical personnel to potentially harmful radiation such as X-ray. Because of its high quality images, MRI is the favoured imaging technique of soft tissue and organs and it allows for the discrimination between normal and diseased tissue, for instance tumours and lesions.

MRI may be carried out with or without MR contrast agents. However, contrast-enhanced MRI usually enables the detection of much smaller tissue changes which makes it a powerful tool for the detection of early stage tissue changes like for instance small tumours or metastases.

Several types of contrast agents have been used in MRI. Water-soluble paramagnetic metal chelates, for instance gadolinium chelates like Omiscan™ (GE Healthcare) are widely used MR contrast agents. Because of their low molecular weight they rapidly distribute into the extracellular space (i.e. the blood and the interstitium) when administered into the vasculature. They are also cleared relatively rapidly from the body.

Blood pool MR contrast agents on the other hand, for instance superparamagnetic iron oxide particles, are retained within the vasculature for a prolonged time. They have proven to be extremely useful to enhance contrast in the liver but also to detect capillary permeability abnormalities, e.g. "leaky" capillary walls in tumours which are a result of tumour angiogenesis.

Despite the undisputed excellent properties of the aforementioned contrast agents their use is not without any risks. Although paramagnetic metal chelates have usually high stability constants, it is possible that toxic metal ions are released in the body after administration. Further, these type of contrast agents show poor specificity.

WO-A-99/35508 discloses a method of MR investigation of a patient using a hyperpolarised solution of a high $T_1$ agent as MRI contrast agent. The term "hyperpolarisation" means enhancing the nuclear polarisation of NMR active nuclei present in the high $T_1$ agent, i.e. nuclei with non-zero nuclear spin, preferably $^{13}$C- or $^{15}$N-nuclei, to a level over that found at room temperature and 1 T (thermal polarisation). Upon enhancing the nuclear polarisation of NMR active nuclei, the population difference between excited and ground nuclear spin states of these nuclei is significantly increased and thereby the MR signal intensity is amplified by a factor of hundred and more. When using a hyperpolarised $^{13}$C- and/or $^{15}$N-enriched high $T_1$ agent, there will be essentially no interference from background signals as the natural abundance of $^{13}$C and/or $^{15}$N is negligible and thus the image contrast will be advantageously high. The main difference between conventional MRI contrast agents and these hyperpolarised high $T_1$ agents is that in the former changes in contrast are caused by affecting the relaxation times of water protons in the body whereas the latter class of agents can be regarded as non-radioactive tracers, as the signal obtained arises solely from the agent.

A variety of possible high $T_1$ agents for use as MR imaging agents are disclosed in WO-A-99/35508, including non-endogenous and endogenous compounds like acetate, pyruvate, oxalate or gluconate, sugars like glucose or fructose, urea, amides, amino acids like glutamate, glycine, cysteine or aspartate, nucleotides, vitamins like ascorbic acid, penicillin derivates and sulphonamides. It is further stated that intermediates in metabolic cycles such as the citric acid cycle like fumaric acid and pyruvic acid are preferred imaging agents for MR imaging of metabolic activity.

Hyperpolarised MR imaging agents that play a role in the metabolic processes in the human and non-human animal body are of great interest, as these hyperpolarised imaging agents can be used to get information about the metabolic state of a tissue in an in vivo MR investigation, i.e. they are useful for in vivo imaging of metabolic activity. Information of the metabolic status of a tissue might for instance be used to discriminate between healthy and diseased tissue.

Pyruvate is a compound that plays a role in the citric acid cycle and the conversion of hyperpolarised $^{13}$C-pyruvate to hyperpolarised $^{13}$C-lactate, hyperpolarised $^{13}$C-bicarbonate and hyperpolarised $^{13}$C-alanine can be used for in vivo MR studying of metabolic processes in the human body. Hyperpolarised $^{13}$C-pyruvate may for instance be used as an MR imaging agent for in vivo tumour imaging as described in detail in WO-A-2006/011810 and for assessing the viability of myocardial tissue by MR imaging as described in detail in WO-A-2006/054903.

It has to be stressed that the signal of a hyperpolarised imaging agent decays due to relaxation and—upon administration to the patient's body—dilution. Hence the $T_1$ value of the imaging agents in biological fluids (e.g. blood) must be sufficiently long to enable the agent to be distributed to the target site in the patient's body in a highly hyperpolarised state. Apart from the imaging agent having a high $T_1$ value, it is extremely important and favourable to achieve a high polarisation level.

Several hyperpolarising techniques are disclosed in WO-A-99/35508, one of them is the dynamic nuclear polarisation (DNP) technique whereby polarisation of MR active nuclei in a sample is effected by a polarisation agent or so-called DNP agent, a compound comprising unpaired electrons. During the DNP process, energy, normally in the form of microwave radiation, is provided, which will initially excite the DNP agent. Upon decay to the ground state, there is a transfer of polarisation from the unpaired electron of DNP agent to the NMR active nuclei of the sample. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. The DNP technique is for example described in WO-A-98/58272 and in WO-A-01/96895, both of which are included by reference herein.

The DNP agent plays a decisive role in the DNP process as its choice has a major impact on the level of polarisation that can be achieved. A variety of DNP agents—in WO-A-99/35508 denoted "OMRI contrast agents"—is known. The use of oxygen-based, sulphur-based or carbon-based stable trityl radicals as described in WO-A-99/35508, WO-A-88/10419, WO-A-90/00904, WO-A-91/12024, WO-A-93/02711, WO-A-98/39277 and WO-A-96/39367 as DNP agents has resulted in high levels of polarisation in a variety of different substances.

It has also been found that for the transfer of polarisation from the DNP agent to the NMR active nuclei of the sample during the DNP process it is necessary that DNP agent and sample are in intimate contact. This intimate contact can be achieved by choosing a DNP agent that is soluble in the sample to be polarised. Further, it is important to prevent crystallization of the DNP agent/sample mixture upon cooling/freezing. It has been found that polarisation levels in samples which crystallize upon cooling/freezing are low or that even no enhancement over the level of the thermal polarisation, i.e. the natural polarisation of a sample at room temperature before the start of the dynamic nuclear polarisation process, could be obtained. It has further been found that polarisation levels in samples which crystallize upon cooling/freezing can be improved by adding glass formers as a DNP agent/sample/glass former mixture forms an amorphous solid ("glass") upon cooling/freezing.

Suitable glass formers are for instance glycerol, propanediol or glycol. However, the addition of glass formers has usually to be kept to the necessary minimum as this addition "dilutes" the sample which is a disadvantage for certain applications like the use of the hyperpolarised sample as an imaging agent in MRI. In this case the hyperpolarised sample needs to be administered to the patient at a high concentration, i.e. a highly concentrated sample must be used in the DNP process. In this context, it is also important that the mass of the frozen composition containing the sample (i.e. DNP agent, sample and if necessary glass formers and/or solvents) is kept as small as possible as a high mass will have a negative impact on the efficiency of the dissolution process, if dissolution is used to transfer the solid hyperpolarised composition after the DNP process into the liquid state, e.g. for using it as an imaging agent. Further, if the polarised sample is intended to be used as an imaging agent, the addition of glass formers might require removal of these compounds before the imaging agent is administered into a patient. Another disadvantage of adding glass formers is that often a decreased solubility of the polarised sample in aqueous carriers is observed. Aqueous carriers are the preferred dissolution media for a hyperpolarised sample intended to be used as an MR imaging agent.

A considerably large number of metabolically active compounds are carboxylates, i.e. salts of carboxylic acids. Examples are pyruvate, lactate, bicarbonate, succinate, malate, fumarate, citrate, isocitrate, a-ketoglutarate, or oxaloacetate. These compounds are readily (commercially) available in form of their sodium salts and most of them can be dissolved in water and mixed with a DNP agent to prepare a composition for the DNP process. However, upon cooling/freezing, these mixtures may crystallize which—without the addition of glass formers—leads to polarisation levels which are too low to use the polarised carboxylates as MR imaging agents for MR imaging of metabolic activity. Some of the aforementioned compounds like pyruvate and lactate may be polarised in form of their acids since these acids do not crystallize upon cooling/freezing and hence the addition of glass formers is not necessary. The disadvantage is that the DNP agent has to be stable and miscible in these acids, criteria which considerably narrow the range of suitable DNP agents. Further, during the dissolution step or afterwards, a base has to be used to convert the free acid into the carboxylate. This also requires consumables (vessels, bottles, tubing etc.) that can withstand strong acids and bases.

We have now found a method to polarise carboxylates without the addition of glass formers. It has been found that carboxylates of organic amines and amino compounds can undergo dynamic nuclear polarisation without the addition of glass formers to the mixture to be polarised, since these carboxylates do not crystallize upon cooling/freezing. The advantage of using carboxylates in the form of their salts with organic amines and amino compounds is, that no glass formers have to be added to the mixture to be polarised and thus the "dilution" of the polarised compound and the removal of the glass formers from the polarised sample is no longer an issue. Thus, a much higher concentration of carboxylate can be used in the DNP process. A further advantage of the direct polarisation of carboxylates is that the indirect route of polarising the free carboxylic acid and all the disadvantages of this route as outlined in the paragraph above can be avoided. This results in the possibility to use a broader range of DNP agents as these agents no longer have to be stable in the acids.

Thus viewed form one aspect the invention provides a method of producing a solid hyperpolarised carboxylate of an organic amine or amino compound, the method comprising preparing a composition comprising a carboxylate of an organic amine or amino compound and a DNP agent and carrying out dynamic nuclear polarisation on the composition.

The term "carboxylate" denotes a molecular entity or entities (e.g. mixtures of different carboxylates) to be hyperpolarised by dynamic nuclear polarisation.

The terms "hyperpolarised" and "polarised" are used interchangeably hereinafter and denote a nuclear polarisation level in excess. Preferably, the terms "hyperpolarised" and "polarised" denote a nuclear polarisation level in excess of 0.1%, more preferably in excess of 1% and most preferably in excess of 10%.

The level of polarisation may for instance be determined by solid state NMR measurements of the NMR active nucleus in the hyperpolarised sample. For instance, if the NMR active nucleus in the hyperpolarised sample is $^{13}$C, a solid state $^{13}$C-NMR of said sample is acquired. The solid state $^{13}$C-NMR measurement preferably consists of a simple pulse-acquire NMR sequence using a low flip angle. The signal intensity of the hyperpolarised sample is compared with the polarisation level of the sample before the dynamic nuclear polarisation process. The level of polarisation is then calculated from the ratio of the signal intensities of sample before and after DNP.

In a similar way, the level of polarisation for dissolved hyperpolarised samples may be determined by liquid state NMR measurements of the NMR active nucleus in the hyperpolarised sample. Again the signal intensity of the dissolved hyperpolarised sample is compared with the polarisation level of the dissolved sample before the dynamic nuclear polarisation process. The level of polarisation is then calculated from the ratio of the signal intensities of sample before and after DNP.

The term "carboxylate of an organic amine or amino compound" denotes a salt of a carboxylic acid and an organic amine or amino compound, preferably a pH neutral salt. The carboxylate in the context of the present invention may be a salt of a monocarboxylic acid like for instance carbonic acid, acetic acid, palmitic acid, oleic acid, pyruvic acid or lactic acid. In another embodiment, the carboxylate may be a salt of a di- or polycarboxylic acid like for instance malic acid, fumaric acid, succinic acid, malonic acid or citric acid. In case of the carboxylate being a salt of a di- or polycarboxylic acid, the salt may be a monocarboxylate, dicarboxylate or a polycarboxylate. For instance in case of citric acid, a tricarboxylic acid, the carboxylate may be a (mono)citrate, i.e. having 2 free carboxylic groups, a dicitrate, i.e. having 1 free carboxylic group or a tricitrate, i.e. having no free carboxylic groups. If the carboxylate used in the method of the invention is a carboxylate of a di- or polycarboxylic acid, it is preferred that the carboxylate does not have any free carboxylic groups.

Preferred carboxylates are drug candidates, preferably small molecules e.g. less than 2000 Da, or a mixture of several drug candidates and the hyperpolarised drug candidate(s) may be used in NMR assays to for instance determine binding affinity to a certain receptor or in enzyme assays. Such assays are described in WO-A-2003/089656 or WO-A-2004/051300 and they are preferably based on the use of liquid state NMR spectroscopy which means that the hyperpolarised solid composition containing the drug candidate(s) has to be liquefied after polarisation, preferably by dissolving or melting it. The carboxylate may or may not be isotopically enriched.

In another preferred embodiment, the carboxylate is an MR imaging agent and the hyperpolarised carboxylate is intended to be used as imaging agent in MR imaging and/or chemical shift imaging. Here, preferred carboxylates are endogenous carboxylates, more preferably endogenous carboxylates that play a role in a metabolic process in the human or non-human animal body. Preferred carboxylates in this context are malate, acetate, fumarate, lactate, citrate, pyruvate, bicarbonate, malonate, succinate, oxaloacetate, α-ketoglutarate, glutamate, aspartate, and isocitrate. Most preferred carboxylates are acetate, fumarate, glutamate, aspartate and pyruvate.

If endogenous carboxylates that play a role in a metabolic process in the human or non-human animal body are used in the method of the invention, these hyperpolarised carboxylates are preferably used as MR imaging agents for in vivo molecular MR imaging and/or chemical shift imaging of metabolic activity in the human or non-human animal body. Of these carboxylates, those are preferred which contain polarised nuclei that exhibit slow longitudinal relaxation so that polarisation is maintained for a sufficient length of time for transfer into a human or non-human animal body and subsequent imaging. Preferred carboxylates contain nuclei with longitudinal relaxation time constants ($T_1$) that are greater than 10 seconds, preferably greater than 30 seconds and even more preferably greater that 60 seconds at a magnetic field strength of 0.01 to 5 T and a temperature in the range of from 20 to 40° C.

Generally, a carboxylate intended to be used as an imaging agent for in vivo MR imaging and/or chemical shift imaging is preferably an isotopically enriched carboxylate, the isotopic enrichment being more preferably an isotopic enrichment of non-zero spin nuclei (MR active nuclei), suitably $^{15}N$—if present in the carboxylate moiety of the carboxylate of an organic amine or amino compound- and/or $^{13}C$, more preferably $^{13}C$. The isotopic enrichment may include either selective enrichments of one or more sites within the carboxylate or uniform enrichment of all sites. Enrichment can for instance be achieved by chemical synthesis or biological labelling, both methods are known in the art and appropriate methods may be chosen depending on the specific carboxylate to be isotopically enriched.

A preferred embodiment of a carboxylate that is intended to be used as an MR imaging agent is a carboxylate that is isotopically enriched in only one position of the molecule, preferably with an enrichment of at least 10%, more suitably at least 25%, more preferably at least 75% and most preferably at least 90%. Ideally, the enrichment is 100%.

The optimal position for isotopic enrichment is dependent on the relaxation time of the MR active nuclei. Preferably, carboxylates are isotopically enriched in positions with long $T_1$ relaxation time. $^{13}C$-enriched carboxylates that are enriched at a carboxyl-C-atom, a carbonyl-C-atom or a quaternary C-atom are preferably used.

Especially preferred carboxylates for use as MR imaging agents are $^{13}C$-pyruvate, $^{13}C$-acetate, $^{13}C$-lactate, $^{13}C$-bicarbonate, $^{13}C$-3-hydroxybutyrate, $^{13}C$-fumarate and $^{13}C$-carbonate with $^{13}C$-pyruvate being most preferred. $^{13}C$-pyruvate may be isotopically enriched at the C1-position ($^{13}C_1$-pyruvate), at the C2-position ($^{13}C_2$-pyruvate), at the C3-position ($^{13}C_3$-pyruvate), at the C1- and the C2-position ($^{13}C_{1,2}$-pyruvate), at the C1- and the C3-position ($^{13}C_{1,3}$-pyruvate), at the C2- and the C3-position ($^{13}C_{2,3}$-pyruvate) or at the C1-, C2- and C3-position ($^{13}C_{1,2,3}$-pyruvate). The C1-position is the preferred one for the $^{13}C$ isotopic enrichment.

In another preferred embodiment, the carboxylate of the method of the invention is used in solid state NMR spectroscopy. Here the hyperpolarised solid carboxylate may be analysed by either static or magic angle spinning solid state NMR spectroscopy. In this embodiment, the carboxylate not limited to carboxylates with certain properties and molecules of any size and type with a carboxylate group can be used as carboxylates in the method of the invention.

As mentioned earlier, the term "carboxylate of an organic amine or amino compound" denotes a salt of a carboxylic acid and an organic amine or amino compound. Amines in the context of the invention may be primary amines, secondary amines or tertiary amines. Due to the free electron pair at the nitrogen atom, amines can react with carboxylic acids to form salts comprising carboxylate anions and quaternary ammonium cations. Amino compounds in the context of the invention are organic chemical compounds that comprise an amino group which can be an unsubstituted amino group, i.e. —$NH_2$, or a substituted amino group, i.e. —NHR or —$NR_2$, wherein R denotes any residue apart from H. Amino compounds may contain other functional groups like hydroxyl groups, carboxyl groups, carbonyl groups or sulphonic acid groups. In the context of the invention, amino compounds should be chosen that readily form salts with the chosen carboxylic acid but that do not form other unwanted by-products. Preferred amino compounds are amines, aminoalcohols, i.e. amino compounds comprising a hydroxyl group, and aminosulphonic acids, most preferred amino compounds are aminoalcohols.

Preferred organic amines or amino compounds in the method of the invention are small molecules of low molecular weight. The lower the molecular weight of the amine or amino compound, the higher the concentration of carboxylate of the organic amine or amino compound in the composition to undergo polarisation. Preferred are organic amines and amino compounds with a molecular weight of 30 to 300 g/mol, more preferred 30 to 200 g/mol and most preferred 30 to 160 g/mol. Suitable low molecular weight organic amines are for instance methylamine, ethylamine, diethylamine, trimethylamine, imidazole or ethylenediamine. Suitable low molecular weight amino compounds are ethanolamine, diethanolamine, triethanolamine, aminopropanediol, 2-amino-2-methyl-1,3-propanediol, tris-(hydroxymethyl) methylamine (TRIS), lysine, N-methyl-D-glucamine, or N-(2-acetamido)-2-aminomethane sulphonic acid, of those compounds, ethanolamine, diethanolamine, triethanolamine, aminopropanediol, 2-amino-2-methyl-1,3-propanediol, N-methyl-D-glucamine and tris(hydroxymethyl)-methylamine (TRIS) are preferred.

If the hyperpolarised carboxylate is intended for use as MR imaging agent, it is important to have a high concentration of the carboxylate in the composition to be polarised, as the hyperpolarised carboxylate needs to be administered to the patient in relatively high concentrations. Further, it is advantageous to keep the mass of the composition to be polarised as small as possible and at the same time have a high concentration of the carboxylate in the composition. This again may be achieved by choosing an amine or amino compound of low molecular weight. If the mass of the composition to be polarised can be kept small, the dissolution of the hyperpolarised composition after polarisation—e.g. in case the hyperpolarised carboxylate is used in liquid NMR or MR imaging—can be carried out more efficiently.

For hyperpolarised carboxylates being used as MR imaging agents it is preferred to choose an organic amine or amino compound that is physiologically tolerable, since such a compound needs not necessarily to be removed—e.g. exchanged by another physiologically tolerable cation—from the hyperpolarised carboxylate before its administration to a patient. In this case physiologically tolerable amino compounds are preferred and in a more preferred embodiment, physiologically tolerable aminoalcohols, aminocarboxylic acids or aminosulphonic acids are used, most preferably physiologically tolerable aminoalcohols.

Preferred aminoalcohols are tris(hydroxymethyl)methylamine (TRIS) and N-methyl-D-glucamine (meglumine). Both are well-known physiologically tolerable compounds; meglumine is used as a cation in ionic preparations of several X-ray and MR contrast agents while TRIS is used as a buffer in liquid formulations of therapeutics and diagnostic agents to be used in or applied to human or non-human animal beings.

Preferred aminosulphonic acids are those comprising hydroxyl groups, preferably N-2-hydroxyethylpiperazine-N'-2-ethanesulfonic acid (HEPES), more preferably N-tris(hydroxymethyl)-2-aminoethanesulfonic acid (TES), 4-(2-hydroxyethyl)-1-piperazin-3-propane-sulfonic acid (HEPPS), N-(2-acetamido)-2-aminoethanesulfonic acid (ACES), 1,4-piperazine-bis-ethanesulfonic acid (PIPES), N,N-bis(2-hydroxyethyl)-2-amino-ethanesulfonic acid (BES) and 3-(N-morpholino)propane-sulphonic acid (MOPS).

In a preferred embodiment of the method of the invention, a pH neutral carboxylate of an organic amine or amino compound is used. To obtain such a pH neutral carboxylate, an organic amine or amino compound is combined with a carboxylic acid in such a molar ratio that all the carboxyl groups present in the carboxylic acid are converted to carboxylates, i.e. in a molar ratio that results in a pH neutral carboxylate of an organic amine or amino compound. If for instance pyruvic acid is reacted with the aminoalcohol TRIS, a 1:1 molar ratio of pyruvic acid and TRIS will result in a TRIS-pyruvate of about pH 5. Hence a slight excess of TRIS has to be used to obtain a pH neutral TRIS-pyruvate.

To obtain the carboxylate of an organic amine or amino compound used in the method of the invention, an organic amine or amino compound is combined with a carboxylic acid, for instance by adding the organic amine or amino compound to the carboxylic acid. This could be done by slowly adding the organic amine or amino compound to a reaction vessel containing the carboxylic acid. The reaction mixture may be stirred to ensure proper mixing of the compounds and the reaction vessel may be cooled. In another embodiment, the organic amine or amino compound and the carboxylic acid may be added to a solution of the DNP agent, preferably a solution of the DNP agent in water. Further, the carboxylic acid and or organic amine or amino compound may be dissolved in a solvent, e.g. water; however, the amount of solvent should be kept to a minimum. The dissolved carboxylic acid and organic amine or amino compound may also be mixed by running the solutions from 2 vessels into a T-piece which ensures mixing. If necessary, means for pumping the solutions through from the vessels through lines/tubing into the T-piece may be used. In yet another embodiment, a salt of the carboxylic acid, e.g. the sodium salt may be dissolved in a solvent like water and passed through an ion exchange column charged with the quaternary ammonium salt of the organic amine or amino compound. This procedure may be more convenient when isotopically labelled carboxylates are used in the method of the invention since these sodium salts are more often readily commercially available whereas the free carboxylic acids are not. Further, since heat generation and prolonged contact of the compounds are avoided, the formation of unwanted by-products is greatly reduced. To keep the amount of solvent to a minimum, the solvent may be evaporated to the wanted volume after production of the carboxylate by methods known in the art.

In a preferred embodiment, the composition to be polarised is a liquid composition, more preferably a dissolved composition, i.e. a solution of a carboxylate of an organic amine or amino compound and the DNP in a solvent or a solvent mixture. The term "solvent" hereinfurther denotes solvents and solvent mixtures. The solvent is chosen such that the carboxylate and the DNP agent are soluble in said solvent. Further, if the hyperpolarised carboxylate is used as an MR imaging agent the solvent is preferably a physiologically tolerable solvent like a pharmaceutically accepted aqueous carrier, e.g. a buffer solution or saline or more preferably water. In a preferred embodiment, the solvent is kept to the minimum which is necessary to result in a dissolved composition.

The composition to be polarised in the method of the invention further comprises a DNP agent, which is essential in the DNP method. To achieve a high polarisation level in the carboxylate to be polarised, the DNP agent has to be stable and soluble in the (dissolved) carboxylate. In this context, stable trityl radicals are the preferred DNP agents and such stable oxygen-based, sulphur-based or carbon-based trityl radicals are for instance described in WO-A-99/35508, WO-A-88/10419, WO-A-90/00904, WO-A-91/12024, WO-A-93/02711, WO-A-96/39367, WO-A-98/39277 and WO-A-2006/011811.

The optimal choice of the DNP agent depends on several aspects. As mentioned before, the DNP agent and the carboxylate must be in intimate contact in order to result in optimal polarisation levels in the carboxylate. Thus, in a preferred embodiment the DNP agent is soluble in the (dissolved) carboxylate. If the carboxylate to be polarised is a lipophilic (hydrophilic) compound, the DNP agent should be lipophilic (hydrophilic) too. If the DNP agent is a trityl radical, lipophilicity or hydrophilicity of said trityl radical can be influenced by choosing suitable lipophilic or hydrophilic residues. Further, the DNP agent has to be stable in presence of the carboxylate. Hence if the carboxylate contains reactive groups, a DNP agent should be used which is relatively inert towards these reactive groups. From the aforesaid it is apparent that the choice of the DNP agent is highly dependent on the chemical nature of the sample.

In a preferred embodiment of the method according to the invention, the carboxylate is pyruvate, more preferred $^{13}C$-pyruvate and most preferred $^{13}C_1$-pyruvate and the organic amine or amino compound is TRIS or meglumine. In this case, the DNP agent is preferably a trityl radical of the formula (1)

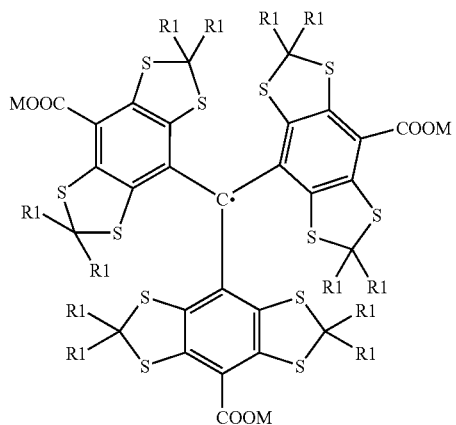

(1)

wherein
- M represents hydrogen or one equivalent of a cation; and
- R1 which is the same or different represents a straight chain or branched $C_1$-$C_6$-alkyl group, $C_1$-$C_6$-hydroxyalkyl group or a group —$(CH_2)_n$—X—R2, wherein n is 1, 2 or 3;
- X is O or S and R2 is a straight chain or branched $C_1$-$C_4$-alkyl group.

In a preferred embodiment, M represents hydrogen or one equivalent of a physiologically tolerable cation. The term "physiologically tolerable cation" denotes a cation that is tolerated by the human or non-human animal living body. Preferably, M represents hydrogen or an alkali cation, an ammonium ion or an organic amine ion, for instance meglumine. Most preferably, M represents hydrogen or sodium.

In a further preferred embodiment, R1 is the same, more preferably a straight chain or branched $C_1$-$C_4$-alkyl group, most preferably methyl, ethyl or isopropyl or a $C_1$-$C_4$-hydroxyalkyl group, most preferably hydroxymethyl or hydroxyethyl.

In a further preferred embodiment, R1 is the same or different, preferably the same and represents —$CH_2$—$OCH_3$, —$CH_2$—$OC_2H_5$, —$CH_2$—$CH_2$—$OCH_3$, —$CH_2$—$SCH_3$, —$CH_2$—$SC_2H_5$ or —$CH_2$—$CH_2$—$SCH_3$, most preferably —$CH_2$—$CH_2$—$OCH_3$.

Such trityl radicals may be synthesized as described in detail in WO-A-88/10419, WO-A-90/00904, WO-A-91/12024, WO-A-93/02711, WO-A-96/39367, WO-A-98/39277 and WO-A-2006/011811.

The composition comprising a carboxylate of an organic amine or amino compound and a DNP agent may be obtained by combining the carboxylate, if necessary dissolved in a solvent, preferably in water and the DNP agent to form a homogenous mixture. In another embodiment, the DNP agent is dissolved in a solvent, preferably in water and the carboxylic acid and organic amine or amino compound are added to this solution, preferably in alternating portions, to form the carboxylate in situ. Intimate mixing of the compounds can be promoted by several means known in the art, such as stirring, vortexing or sonication.

In a preferred embodiment, the composition used in the method of the invention further comprises a paramagnetic metal ion. The presence of paramagnetic metal ions in the composition to be polarised is preferred since it leads to increased polarisation levels in the carboxylate.

The paramagnetic metal ion comprised in the composition used in the method of the invention is a paramagnetic metal ion of a lanthanide metal of atomic numbers 58-70 or of a transition metal of atomic numbers 21-29, 42 or 44. Paramagnetic metal ions of one or different metals may be used in the method of the invention. Preferably, paramagnetic metal ions of one metal are used. Suitable paramagnetic ions include for instance $Cr^{3+}$, $Mn^{2+}$, $Fe^{3+}$, $Fe^{2+}$, $Co^{2+}$, $Ni^{2+}$, $Cu^{2+}$, $Nd^{3+}$, $Sm^{3+}$, $Gd^{3+}$, $Tb^{3+}$, $Dy^{3+}$, $Ho^{3+}$, $Er^{3+}$, and $Yb^{3+}$. In a preferred embodiment the paramagnetic metal ion is chosen from the group consisting of $Cr^{3+}$, $Mn^{2+}$, $Fe^{3+}$, $Fe^{2+}$, $Gd^{3+}$ and $Tb^{3+}$, in a more preferred embodiment from the group consisting of $Cr^{3+}$, $Mn^{2+}$, $Fe^{3+}$ and $Gd^{3+}$.

Suitably, the paramagnetic metal ions are used in chelated form or in the form of their salts.

If the carboxylate to be polarised is intended to undergo solid state NMR, paramagnetic metal ions are preferably used in form of their salts. Suitable salts are for example $CrCl_3$, $MnCl_2$, $FeCl_2$, $FeCl_3$, $GdCl_3$ or paramagnetic metal carboxylates, preferably carboxylates which are those that are polarised. Hence if the carboxylate to be polarised is acetate, the paramagnetic metal ion would preferably be a paramagnetic metal acetate, for instance Fe(III)acetate. Likewise, if the carboxylate to be polarised is pyruvate, the paramagnetic metal ion would preferably be a paramagnetic metal pyruvate, for instance Gd(III)pyruvate. It is of advantage to select a salt that is soluble in the carboxylate or a solution of the carboxylate. In another embodiment, the paramagnetic metal ions may be added in chelated form.

For liquid state NMR or use as an imaging agent in a living human or animal body, the solid hyperpolarised carboxylate obtained by the method of the invention has to be dissolved or melted to result in a solution or liquid. However, free paramagnetic ions in such a solution or liquid dramatically shorten the $T_1$ relaxation time of the polarised nuclei in the sample, i.e. accelerating the natural decay of the polarisation and thus shortening the time the carboxylate will provide high MR signal intensities. On the other hand, if the carboxylate to be polarised is intended to be used as an imaging agent in a living human or animal body free paramagnetic metal ions—if not removed from the final injectable—often are not or poorly physiologically tolerated and thus have unwanted effects, e.g. toxic effects.

To overcome the aforementioned effects of free paramagnetic metal ions, the paramagnetic metal ions may be used in chelated form. The advantage is that the removal of the paramagnetic chelate from the liquid hyperpolarised carboxylate does not have to be carried out under such high time pressure to avoid $T_1$ shortening as discussed above. By using a carboxylate of an organic amine or amino compound according to the method of the invention instead of polarising the free carboxylic acid, it is also possible to use a considerably wider range of paramagnetic chelates, most of which would not be stable in a free carboxylic acid due to protonation of the nitrogen atoms and carboxylic groups commonly present in the chelating agents.

The aforementioned effects can further be overcome by using paramagnetic metal ions in form of their salts and rapidly removing the paramagnetic metal ions after dissolving or melting the hyperpolarised carboxylate. Methods for the removal of paramagnetic metal ions are disclosed later in this application.

In another embodiment, the aforementioned effects can be overcome by using paramagnetic metal ions in form of their salts and adding chelating agents to the dissolution medium to rapidly complex free paramagnetic metal ions. In this case a chelating agent should be chosen that is soluble and stable in the dissolution medium and that rapidly forms a stable complex with the free paramagnetic metal ion.

As stated above, paramagnetic metal ions may be used in the method of the invention in chelated form. The term "paramagnetic chelate" herein further denotes paramagnetic metal ions in chelated form, i.e. complexes of paramagnetic metal ions and chelating agents.

A variety of chelating agents is known for this purpose. Generally, cyclic and acyclic chelating agents often containing heteroatoms like N, O, P or S may be used with cyclic chelating agents being the preferred ones. Suitable acyclic chelating agents are for instance DTPA and compounds thereof like DTPA-BMA, DTPA-BP, DTPA-BMEA, EOB-DTPA, BOPTA and MS-325, EDTA and compounds thereof like EDTA-BMA, DPDP, PLED, HPTA, amides or diamides like TOGDA, cryptands or sulphonates. Suitable cyclic chelating agents are for instance PCTA-[12], PCTP-[12], PCTP-[13], DOTA, DO3A and compounds thereof like HP-DO3A and DO3A-butriol. DOTA, DO3A and compounds thereof are preferred cyclic chelating agents. These chelating agents are known in the art and the skilled artisan is able to find extensive literature on these chelating agents and their preparation.

In another embodiment, chelating agents are used that are relatively inert chemical entities, for instance fullerenes or zeolites. Such chelating agents which do encage or encapsulate a paramagnetic metal ion are preferred if the carboxylate to be polarised comprises reactive functional groups that could react with more reactive chelating agents, e.g. like those mentioned in the previous paragraph.

In the method of the invention, the paramagnetic chelates may either be a monomeric paramagnetic chelate, i.e. a chemical entity consisting of a chelating agent and a single paramagnetic metal ion or a multimeric paramagnetic chelate, i.e. a chemical entity consisting of two or more subunits wherein each subunit consists of a chelating agent and a single paramagnetic metal ion. An example of a trimeric paramagnetic chelate is 1,3,5-tris-(N-(DO3A-acetamido)-N-methyl-4-amino-2-methylphenyl)-[1,3,5]triazinane-2,4,6-trione, a paramagnetic chelate consisting of a triazinetrione core with 3 subunits connected to said core wherein each subunit comprises $Gd^{3+}$ as the paramagnetic metal ion and a DO3A derivative as the chelating agent. The synthesis of this trimeric paramagnetic chelate is described in the Example part of this application As with the DNP agent described before, the carboxylate to be polarised must be in intimate contact with the paramagnetic metal ion. In the following, unless otherwise stated or specified, the term "paramagnetic metal ion" is used for both paramagnetic metal ions in form of their salts and paramagnetic chelates. If the carboxylate is in solution (i.e. dissolved in a solvent like water), it is preferred to use a paramagnetic metal ion which is soluble in the dissolved carboxylate. Hence, like with the DNP agent, the paramagnetic metal ion and the carboxylate preferably form a homogeneous mixture. If the carboxylate to be polarised is a lipophilic (hydrophilic) compound, the paramagnetic chelate should be lipophilic (hydrophilic) too. Lipophilicity or hydrophilicity of paramagnetic chelates can for instance be influenced by choosing chelating agents that comprise suitable lipophilic or hydrophilic residues. Further, it is preferred that the paramagnetic chelate is stable in presence of the carboxylate as complex dissociation (dechelation) will lead to free paramagnetic ions with detrimental consequences on the polarisation decay and hence polarisation level in a liquefied hyperpolarised carboxylate as described above, unless the free paramagnetic metal ions are rapidly removed after the solid hyperpolarised carboxylate has been liquefied. If the carboxylate to be polarised contains reactive groups a paramagnetic metal ion should be used which is relatively inert towards these reactive groups. From the aforesaid it is apparent that the choice of the paramagnetic metal ion is highly dependent on the chemical nature of the carboxylate and its final use (solid NMR, liquid NMR or imaging agent).

Another aspect of the invention is a method for producing a liquid hyperpolarised carboxylate, the method comprising preparing a composition comprising a carboxylate of an organic amine or amino compound, a DNP agent and optionally a paramagnetic metal ion, carrying out dynamic nuclear polarisation on the composition, liquefying the composition and optionally removing the DNP agent from the liquefied composition.

For carrying out the methods according to the invention, the first step is to prepare a composition comprising a carboxylate of an organic amine or amino compound, a DNP agent and optionally a paramagnetic metal ion.

If the carboxylate used in the method of the invention is in solution, e.g. dissolved in a solvent, preferably in an aqueous carrier or water, the dissolved carboxylate is combined with the chosen DNP agent, preferably a trityl radical and optionally with a paramagnetic metal ion to form a composition where the compounds are in intimate contact. More preferably, the chosen DNP agent and the paramagnetic metal ion are soluble in the dissolved carboxylate. Intimate mixing may be can be further promoted by several means known in the art, such as stirring, vortexing or sonication. In another embodiment, a solution of the DNP agent in a solvent, preferably water, is prepared and alternating portions of the carboxylic acid and the organic amine or amino compound are added to form the carboxylate of the organic amine or amino compound in situ. Optionally, a paramagnetic metal ion is added and dissolved in the solution containing the DNP agent and the carboxylate. In yet another embodiment, a solution of the paramagnetic metal ion, preferably in water, is prepared and alternating portions of the carboxylic acid and the organic amine or amino compound are added to form the carboxylate of the organic amine or amino compound in situ. The DNP agent is subsequently added and dissolved in the solution containing the paramagnetic metal ion and the carboxylate. In yet another embodiment, the DNP agent and the paramagnetic metal ion are dissolved in a solvent, preferably water, either simultaneously or subsequently and alternating portions of the carboxylic acid and the organic amine or amino compound are added to form the carboxylate of the organic amine or amino compound in situ.

If a trityl radical is used as DNP agent, a suitable concentration is of such a trityl radical is 5 to 25 mM, preferably 10 to 20 mM in the composition. If a paramagnetic metal ion is added to the composition, a suitable concentration of such a paramagnetic metal ion is 0.1 to 6 mM (metal ion) in the composition, and a concentration of 0.5 to 4 mM is preferred.

After having prepared the composition, said composition is cooled/frozen. Cooling/freezing may be achieved by methods known in the art, e.g. by freezing the composition in liquid nitrogen or by simply placing it in the DNP polariser, where liquid helium will freeze it.

The composition may be degassed before cooling/freezing. Degassing may be achieved by bubbling helium gas through the composition (e.g. for a time period of 2-15 min) but can be effected by other known common methods.

The DNP technique is for instance described in WO-A-98/58272 and in WO-A-01/96895, both of which are included by reference herein. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. In a preferred embodiment, the DNP process is carried out in liquid helium and a magnetic field of about 1 T or above. Suitable polarisation units (=polarisers) are for instance described in WO-A-02/37132. In a preferred embodiment, the polarisation unit comprises a cryostat and polarising means, e.g. a microwave chamber connected by a wave guide to a microwave source in a central bore surrounded by magnetic field producing means such as a superconducting magnet. The bore extends vertically down to at least the level of a region P near the superconducting magnet where the magnetic field strength is sufficiently high, e.g. between 1 and 25 T, for polarisation of the sample nuclei to take place. The bore for the probe (=composition to be polarised) is preferably sealable and can be evacuated to low pressures, e.g. pressures in the order of 1 mbar or less. A probe introducing means such as a removable transporting tube can be contained inside the bore and this tube can be inserted from the top of the bore down to a position inside the microwave chamber in region P. Region P is cooled by liquid helium to a temperature low enough to for polarisation to take place, preferably temperatures of the order of 0.1 to 100 K, more preferably 0.5 to 10 K, most preferably 1 to 5 K. The probe introducing means is preferably sealable at its upper end in any suitable way to retain the partial vacuum in the bore. A probe-retaining container, such as a probe-retaining cup, can be removably fitted inside the lower end of the probe introducing means. The probe-retaining container is preferably made of a lightweight material with a low specific heat capacity and good cryogenic properties such, e.g. KelF (polychlorotrifluoroethylene) or PEEK (polyetheretherketone) and it may be designed in such a way that it can hold more than one probe.

The probe is inserted into the probe-retaining container, submerged in the liquid helium and irradiated with microwaves, preferably at a frequency about 94 GHz at 200 mW. The level of polarisation may be monitored by for instance acquiring solid state NMR signals of the probe during microwave irradiation, depending on the sample to be polarised. Generally, a saturation curve is obtained in a graph showing NMR signal vs. time. Hence it is possible to determine when the optimal polarisation level is reached.

If the polarised carboxylate is intended for use as a MR imaging agent, the composition containing the carboxylate is transferred from a solid hyperpolarised state to a liquid hyperpolarised state (i.e. liquefied), either by dissolving it after the DNP process in an appropriate solvent or solvent mixture, e.g. a physiologically tolerable and pharmaceutically accepted aqueous carrier like water, a buffer solution or saline or by melting it. Dissolution is preferred and the dissolution process and suitable devices therefore are described in detail in WO-A-02/37132. The melting process and suitable devices for the melting are for instance described in WO-A-02/36005.

In a preferred embodiment, the solid composition containing the hyperpolarised carboxylate of an organic amine or amino compound is dissolved in water or an aqueous buffer solution. In a further preferred embodiment, the carboxylate is a carboxylate of a buffer compound like TRIS, TRICIN or aminosulphonic acids like ACES, PIPES, BES, MPOS, HEPES, TES or HEPPS (all of the mentioned buffer compounds being organic amino compounds within the definition of the invention) and the solid composition is dissolved in water which will result in a buffered solution of the carboxylate.

In a subsequent step, the DNP agent and the optionally present paramagnetic metal ion may be removed from the liquefied composition. If the hyperpolarised carboxylate is intended to be used as a MR imaging agent or for other applications in a living human or animal being, the DNP agent, preferably a trityl radical and the paramagnetic metal ion are preferably removed from the liquefied composition.

Methods usable to partially, substantially or completely remove the trityl radical and the paramagnetic metal ion are known in the art. Generally, the methods applicable depend on the nature of the trityl radical and the paramagnetic metal ion. Upon dissolution of the solid hyperpolarised composition, the trityl radical and/or the paramagnetic metal ion might precipitate and thus may easily be separated from the liquid by filtration.

If no precipitation occurs, the trityl radical and the paramagnetic metal ion may be removed by chromatographic separation techniques, e.g. liquid phase chromatography like reversed phase chromatography, ion exchange chromatography, (solid phase) extraction or other chromatographic separation methods known in the art. In general, it is preferred to use a method which is able to remove both the trityl radical and the paramagnetic metal ion in one step as polarisation in the liquid carboxylate decays due to $T_1$ relaxation. The faster and the more efficient unwanted compounds are removed from the liquid carboxylate the higher the polarisation level retained in the carboxylate. Hence not only from the point of having an intimate contact between carboxylate, trityl radical and paramagnetic metal ion but also from the point of a fast removal it is of benefit to select a trityl radical and a paramagnetic metal ion which have similar chemical properties, e.g. are both lipophilic or hydrophilic chemical compounds. If for instance a lipophilic trityl radical and a lipophilic paramagnetic chelate are used, both compounds could be removed by reversed phase liquid chromatography on a single chromatography column.

If free paramagnetic metal ions are present in the liquefied composition (e.g. due to the use of a paramagnetic metal salt), these ions are preferably removed by using a cation exchange column or ionic imprinted resins as disclosed by O. Vigneau et al., Anal. Chim. Acta 435(1), 2001, 75-82. Another possible method is nano-filtration by selective complexation of free paramagnetic metal ions onto a charged organic membrane, as disclosed by A. Sorin et al., J. Membrane Science 267(1-2), 2005, 41-49. Further, free paramagnetic metal ions may be removed from the liquefied composition by affinity chromatography in analogy to what is disclosed by S. Donald et al. J. Inorg. Biochem. 56(3), 1994, 167-171.

As trityl radicals have a characteristic UV/visible absorption spectrum, it is possible to use UV/visible absorption measurement as a method to check for their presence in the liquid composition after their removal. In order to obtain quantitative results, i.e. the concentration of the trityl radical present in the liquid composition, the optical spectrometer can be calibrated such that absorption at a specific wavelength from a sample of the liquid composition yields the corresponding trityl radical concentration in the sample. Removal of the trityl radical is especially preferred if the liquid hyperpolarised carboxylate is used as an imaging agent for in vivo MR imaging of a human or non-human animal body.

After removal of the paramagnetic metal ion—if having been present in the composition which is polarised—and/or the trityl radical, the liquid sample may be checked for residual paramagnetic metal ion and/or trityl radical.

Fluorescence or UV/visible absorption measurement can be used as a method to check for the presence of paramagnetic chelates, provided that the chelates contain a (strong) chromophore. Another way to check for the presence of paramagnetic chelates is electrochemical detection, provided an electroactive moiety is present in the chelate.

If paramagnetic metal salts were used in the composition, fluorescence measurements may be used to check for free paramagnetic metal ions after their removal from the liquid composition. If for instance a $Gd^{3+}$-salt is used, fluorescence with an excitation wavelength of 275 nm and monitoring of emission at 314 nm may be used as a method to detect free $Gd^{3+}$ with high specificity. Further, free $Gd^{3+}$ can be detected by visible absorbance at 530-550 nm following complexation with the colorimetric agent PAR (4-(2-pyridylazo)resorcinol). Other colorimetric agents suitable for other paramagnetic metal ions are known in the art and can be used in the same way.

In a preferred embodiment of the method according to the invention the composition comprises a $^{13}C$-pyruvate, preferably $^{13}C_1$-pyruvate of TRIS or meglumine, a trityl radical, preferably a trityl radical of formula (I) and either a paramagnetic chelate comprising $Gd^{3+}$ as a paramagnetic metal ion or a $Gd^{3+}$-salt like $GdCl_3$ or Gd-pyruvate. A composition is prepared by preferably dissolving the Gd-chelate or Gd-salt in a solvent, preferably water and adding $^{13}C_1$-pyruvic acid and TRIS or meglumine, preferably in alternating portions, to said solution. In a subsequent step, the trityl radical of formula (1) is added to the solution and the so-obtained composition is cooled/frozen. After dynamic nuclear polarisation, the solid hyperpolarised composition is dissolved in an aqueous carrier, preferably in water.

If a $Gd^{3+}$-salt has been used as paramagnetic metal ion, it is important to remove $Gd^{3+}$ ions from the dissolved $^{13}C$-pyruvate as quick as possible. Suitable methods are the removal by using a cation exchange column or ionic imprinted resins as disclosed by O. Vigneau et al., Anal. Chim. Acta 435(1), 2001, 75-82. Another possible method is nano-filtration by selective complexation of free $Gd^{3+}$ onto a charged organic membrane, as disclosed by A. Sorin et al., J. Membrane Science 267(1-2), 2005, 41-49. Further, free $Gd^{3+}$ may be removed by affinity chromatography as disclosed by S. Donald et al. J. Inorg. Biochem. 56(3), 1994, 167-171. In another embodiment, the dissolution medium comprises one or more compounds which are able to complex free $Gd^{3+}$ ions, e.g. chelating agents like ETDA, DTPA or compounds thereof like DTPA-BMA. The so-obtained Gd-chelates may be removed from the dissolved $^{13}C$-pyruvate as described in the next paragraph.

If a Gd-chelate has been used as paramagnetic metal ion, and a trityl radical of formula (1), the chelate may be removed by using reversed phase liquid chromatography, which allows the simultaneous removal of the trityl radical of formula (1).

Suitable methods to check for residual free $Gd^{3+}$, Gd-chelate and trityl radical of formula (1) in the purified dissolved carboxylate are described on page 22/23.

Liquid hyperpolarised $^{13}C$-pyruvate produced according to the method of the invention may be used as a "conventional" MR imaging agent, i.e. providing excellent contrast enhancement for anatomical imaging. A further advantage of liquid hyperpolarised $^{13}C$-pyruvate produced according to the method of the invention is, that pyruvate is an endogenous compound which is well tolerated by the human body, even in higher concentrations. As a precursor in the citric acid cycle, pyruvate plays an important metabolic role in the human body. Pyruvate is converted into different compounds: its transamination results in alanine, via oxidative decarboxylation pyruvate is converted into acetyl-CoA and bicarbonate, the reduction of pyruvate results in lactate and its carboxylation in oxaloacetate.

Further, the conversion of hyperpolarised $^{13}C$-pyruvate to hyperpolarised $^{13}C$-lactate, hyperpolarised $^{13}C$-bicarbonate (in the case of $^{13}C_1$-pyruvate, $^{13}C_{1,2}$-pyruvate or $^{13}C_{1,2,3}$-pyruvate only) and hyperpolarised $^{13}C$-alanine can be used for in vivo MR studying of metabolic processes in the human body. $^{13}C$-pyruvate has a $T_1$ relaxation in human full blood at 37° C. of about 42 s, however, the conversion of hyperpolarised $^{13}C$-pyruvate to hyperpolarised $^{13}C$-lactate, hyperpolarised $^{13}C$-bicarbonate and hyperpolarised $^{13}C$-alanine has been found to be fast enough to allow signal detection from the $^{13}C$-pyruvate parent compound and its metabolites. The amount of alanine, bicarbonate and lactate is dependent on the metabolic status of the tissue under investigation. The MR signal intensity of hyperpolarised $^{13}C$-lactate, hyperpolarised $^{13}C$-bicarbonate and hyperpolarised $^{13}C$-alanine is related to the amount of these compounds and the degree of polarisation left at the time of detection, hence by monitoring the conversion of hyperpolarised $^{13}C$-pyruvate to hyperpolarised $^{13}C$-lactate, hyperpolarised $^{13}C$-bicarbonate and hyperpolarised $^{13}C$-alanine it is possible to study metabolic processes in vivo in the human or non-human animal body by using non-invasive MR imaging.

It has been found that the MR signal amplitudes arising from the different pyruvate metabolites vary depending on the tissue type. The unique metabolic peak pattern formed by alanine, lactate, bicarbonate and pyruvate can be used as fingerprint for the metabolic state of the tissue under examination and thus allows for the discrimination between healthy tissue and tumour tissue. This makes the composition according to the invention an excellent agent for in vivo MR tumour imaging. The use of pyruvate for tumour imaging has been described in detail in WO-A-2006/011810.

Further, the use of hyperpolarised $^{13}C$-pyruvate for cardiac imaging has been described in WO-A-2006/054903.

Another aspect of the invention is a composition comprising a carboxylate of an organic amine or amino compound, a DNP agent, preferably a trityl radical and optionally a paramagnetic metal ion. In a preferred embodiment, the composition comprises a carboxylate of an organic amine or amino compound, a DNP agent, preferably a trityl radical and a paramagnetic metal ion.

Yet another aspect of the invention are compositions comprising a carboxylate of an organic amine or amino compound, a DNP agent, preferably a trityl radical and optionally a paramagnetic metal ion for use in a dynamic nuclear polarisation. In a preferred embodiment, the composition comprises a carboxylate of an organic amine or amino compound, a DNP agent, preferably a trityl radical and a paramagnetic metal ion for use in a dynamic nuclear polarisation.

Yet another aspect of the invention is a composition comprising a hyperpolarised carboxylate of an organic amine or amino compound, the composition being obtained by dynamic nuclear polarisation.

Yet another aspect of the invention is a composition comprising a hyperpolarised carboxylate of an organic amine or amino compound for use as MR imaging agent, the composition being obtained by dynamic nuclear polarisation Yet another aspect of the invention is a composition comprising a hyperpolarised carboxylate of an organic amine or amino compound, a DNP agent, preferably a trityl radical and optionally a paramagnetic metal ion, the composition being obtained by dynamic nuclear polarisation. In a preferred embodiment, the composition comprises a hyperpolarised carboxylate of an organic amine or amino compound, a DNP agent, preferably a trityl radical and a paramagnetic metal ion, the composition being obtained by dynamic nuclear polarisation.

EXAMPLES

Example 1

Dynamic Nuclear Polarisation of a Composition Containing Sodium $^{13}C_1$-Pyruvate, a Trityl Radical and Water Comparison Example 128.3 mg sodium $^{13}C_1$-pyruvate was dissolved in 244.1 mg water. Tris-(8-carboxy-2,2,6,6-tetra (hydroxyethyl)benzo[1,2-d:4,5d']bis(1,3) dithiole-4-yl)methyl sodium salt which was prepared described in example 7 of WO-A-98/39277 was added to result in a composition being 15.2 mM in trityl radical. The composition was placed in a probe cup and inserted in a DNP polariser. The composition was polarised under DNP conditions at 1.2 K in a 3.35 T magnetic field under microwave irradiation (93.950 GHz). After 2.5 hours, the polarisation was stopped.

Solid state polarisation was determined by solid state $^{13}C$-NMR. The solid state $^{13}C$-NMR measurement consisted of a simple pulse-acquire NMR sequence using a low flip angle. The signal intensity of the dynamic nuclear polarised sample is compared with the thermally polarised sample, i.e. the natural polarisation of the sample at room temperature before the start of the dynamic nuclear polarisation process. The polarisation was calculated from the ratio of the signal intensities of the thermally polarised sample and the dynamic nuclear polarised sample. As a result, the solid state polarisation of the composition was identical with the thermal polarisation of the composition, meaning that the nuclear spin polarisation of the $^{13}C$ nuclei present in the composition could not be enhanced by the DNP polarisation.

Example 2

Dynamic Nuclear Polarisation of a Composition Containing Sodium $^{13}C_1$-Pyruvate, Trityl Radical, a Glass Former and Water Comparison Example 128.3 mg sodium $^{13}C_1$-pyruvate was dissolved in 244.1 mg water and 309.3 mg glycerol was added to make a total volume of 540 µl. 11.2 mg of the trityl radical of Example 1 was added to result in a composition being 15.2 mM in trityl radical. The composition contained 14.6% (w/w) of pyruvate which is most concentrated sodium pyruvate mixture that can be obtained. An aliquot of 102.4 µl of the composition was placed in a probe cup and inserted in a DNP polariser. The composition was polarised under DNP conditions at 1.2 K in a 3.35 T magnetic field under microwave irradiation (93.950 GHz). After 2.5 hours, the polarisation was stopped and the solid composition was dissolved in water containing 100 mg EDTA per liter.

Liquid state polarisation was determined by liquid state $^{13}C$-NMR at 400 MHz to be 9.6%. Hence by adding a glass former the nuclear spin polarisation of the $^{13}C$ nuclei present in the composition could be enhanced by the DNP polarisation.

Example 3

Dynamic Nuclear Polarisation of a Composition Containing TRIS-$^{13}C_1$-Pyruvate, a Trityl Radical and Water 78.4 mg (0.65 mmol) TRIS was mixed with 64.3 mg $^{13}C_1$-pyruvic acid (90% purity, 0.65 mmol) in 51.3 mg water to a clear solution of 160 µl volume. The trityl radical of Example 1 was added to result in a composition being 15.5 mM in trityl radical. The composition contained 30% (w/w) of pyruvate. An aliquot of 136.6 mg of the composition was placed in a probe cup and inserted in a DNP polariser. The composition was polarised under DNP conditions at 1.2 K in a 3.35 T magnetic field under microwave irradiation (93.950 GHz). After 2.5 hours, the polarisation was stopped and the solid composition was dissolved in water containing 100 mg EDTA per liter.

Liquid state polarisation was determined by liquid state $^{13}C$-NMR at 400 MHz to be 10.5%. Hence by preparing a TRIS-$^{13}C_1$-pyruvate the nuclear spin polarisation of the $^{13}C$ nuclei present in the composition could be enhanced by the DNP polarisation to about the same level as in the composition of Example 2. However, the composition of Example 3 contains more than the double amount of pyruvate and if the pyruvate was intended to be used as MR imaging agent, no added glass formers would have to be removed before administration to a patient.

Example 4

Synthesis of the Gd-chelate of 1,3,5-Tris-(N-(DO3A-acetamido)-N-methyl-4-amino-2-methyl-phenyl)-[1,3,5]triazinane-2,4,6-trione (10)

4a) Preparation of 2-Methyl-4-nitrophenylisocyanate (1)

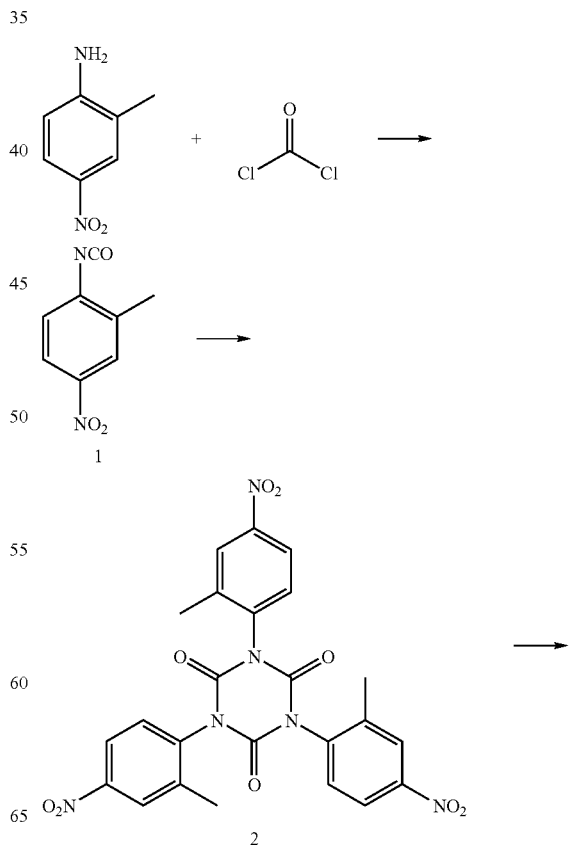

-continued

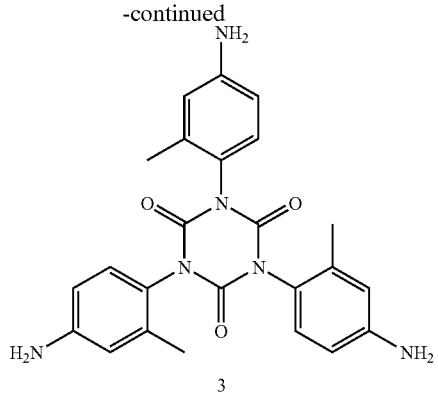

3

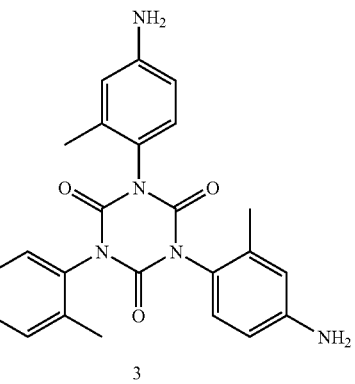

3

2-Methyl-4-nitroaniline (35.0 g, 230 mmol) was dissolved in ethyl acetate (400 ml) and cooled to 0° C. Phosgene (180 ml, 20% in toluene) was added drop wise over 30 min, precipitation of a white salt followed instantly. After the last addition the temperature was allowed to slowly rise to room temperature, and then the reaction mixture was brought to reflux (~100° C.). It was refluxed for 2 h 30 min, after which 200 ml of solvent was distilled off before the temperature was lowered to 80° C. and phosgene (140 ml, 20% in toluene) was added drop wise. After the last addition the reaction solution was refluxed for 3 hours, allowed to cool to room temperature and concentrated to dryness. The brown/yellow material was dissolved in diethyl ether (250 ml), filtered and concentrated to give a pale brown powder (36 g, 88%).

4b) Preparation of 1,3,5-Tris-(4-nitro-2-methyl-phenyl)-[1,3,5]triazinane-2,4,6-trione (2)

To 2-methyl-4-nitrophenylisocyanate (36.0 g) in a 250 ml flask was added DMSO (50 ml) and the flask was sealed with a glass stopper which was kept in place with a plastic clip. The flask was immediately lowered into an oil bath heated to 85° C. and the dark brown reaction solution was heated for 16 h 30 min. The oil bath was removed and the reaction solution was allowed to cool to room temperature before being poured into water (800 ml), sonicated, and the precipitate was filtered off. The filter cake was added to ethanol (500 ml) and was refluxed for 4 hours, then allowed to cool to room temperature and the product was filtered off to give an off-white powder (28.1 g, 78%).

4c) Preparation of 1,3,5-Tris-(4-amino-2-methyl-phenyl)-[1,3,5]triazinane-2,4,6-trione (3)

1,3,5-tris-(4-nitro-2-methyl-phenyl)-[1,3,5]triazinane-2,4,6-trione (2.86 g, 5.4 mmol) was dissolved in THF (70 ml). HCl (4.5 ml, 6M), water (18 ml) and Pd/C (0.6 g, 10%) was added. The reaction vessel was evacuated and filled with argon in three cycles before hydrogenated on a Parr hydrogenation apparatus (60 psi). After 2 hours the excess hydrogen was evacuated with a membrane pump and the Pd/C (10%) was filtered off. The clear reaction solution was concentrated until no more THF remained and the pH adjusted to 7 with NaHCO₃ (~3.7 g). The aqueous phase was extracted with ethyl acetate (3×100 ml) and the combined organic phases were dried with MgSO₄, filtered and concentrated to give a brown powder. The crude product was recrystallized from methanol to give the product as an off-white powder (1.9 g, 80%).

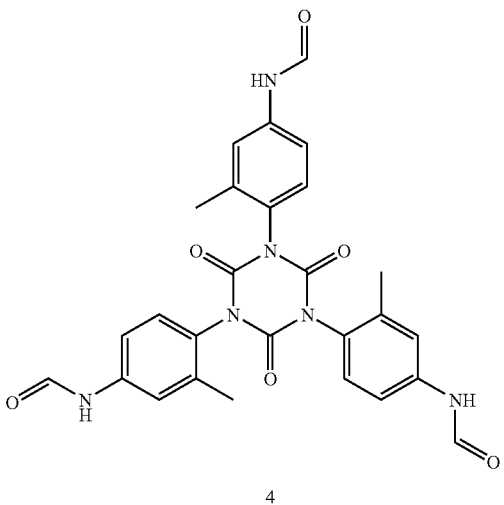

4

4d) Preparation of 1,3,5-Tris-(4-formamido-2-methyl-phenyl)-[1,3,5]triazinane-2,4,6-trione (4)

Formic acid (175 ml) was put in an ice-cooled 500 ml round-bottom flask. Acetic anhydride (15 ml, 0.16 mol) was added and the yellow solution was stirred under argon for 1 h at 0° C. The triamine 3 (8.7 g, 0.020 mol) was added to this solution and the ice bath was removed. After stirring under argon at room temperature for 30 minutes HPLC showed complete reaction. The solvent was removed in vacuo and the brown, sticky residue was suspended in H₂O and filtered off. It was then washed thoroughly with H₂O to make sure all acid was removed. The product was a pale-brown solid (10.2 g, 99%).

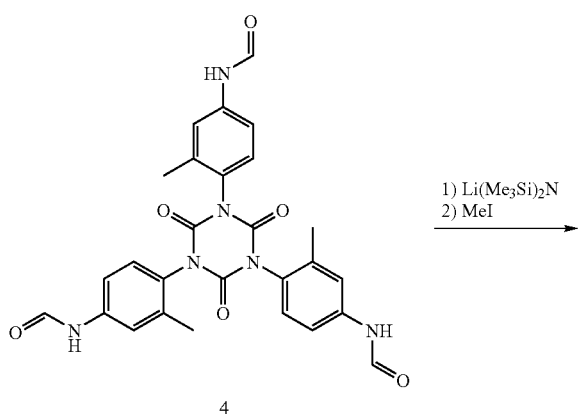

4

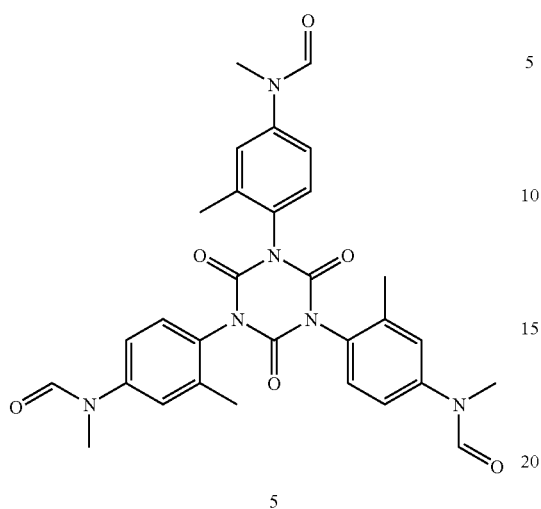

5

4e) Preparation of 1,3,5-Tris-(N-formyl-N-methyl-4-amino-2-methyl-phenyl)-[1,3,5]triazinane-2,4,6-trione (5)

All glassware was carefully dried in oven and DMF was dried over 4 Å molecular sieves. Li(Me$_3$Si)$_2$N (116 ml, 0.116 mol, 1 M in hexane) was added to a DMF-solution (115 ml) of 4 (10.2 g, 0.0193 mol) in 500 ml round-bottom flask. The reaction mixture, which turned from a light brown solution to a brick-red slurry, was stirred under argon for 1 h. Methyl iodide (12.2 ml, 0.196 mol) was added and the reaction mixture was stirred for 2 h or until complete methylation could be shown on HPLC. The hexane was then removed on rotary evaporator and the residue was poured into a solution of NaH$_2$PO$_4$ (1300 ml, 100 mM) under vigorous stirring. The precipitate of 5 formed was filtered off as a pale solid (6.7 g, 60%).

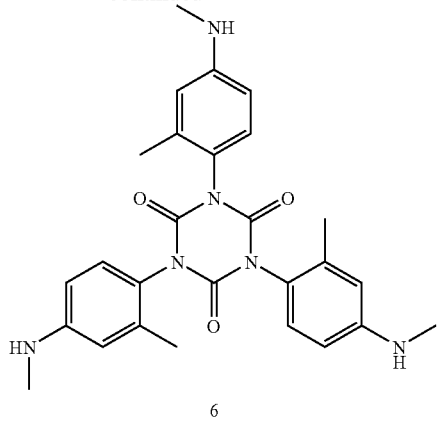

6

4f) Preparation of 1,3,5-Tris-(N-methyl-4-amino-2-methyl-phenyl)-[1,3,5]triazinane-2,4,6-trione (6)

Dioxane (52 ml), HCl (52 ml, 6 M) and 5 (6.5 g, 11 mmol) were mixed in a 250 ml round-bottom flask to form a pale slurry. The reaction mixture was heated to reflux for 30 minutes under argon. The now yellow solution was allowed to cool to room temperature and solvents were then removed on a rotary evaporator. The orange residue was then dissolved in 500 ml H$_2$O and neutralized with a solution of NaHCO$_3$ (sat.) under vigorous stirring. The precipitate formed was filtered off and washed several times with H$_2$O giving a pale solid (4.7 g, 84%).

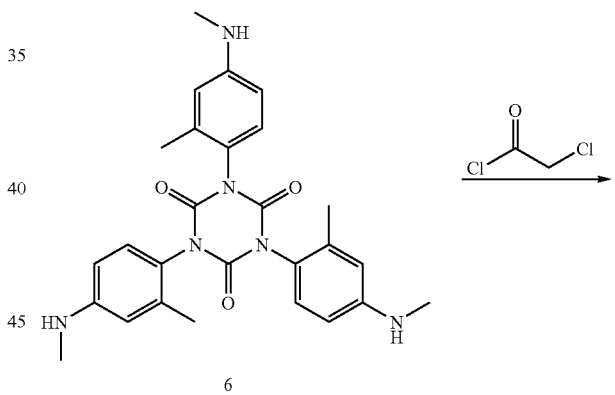

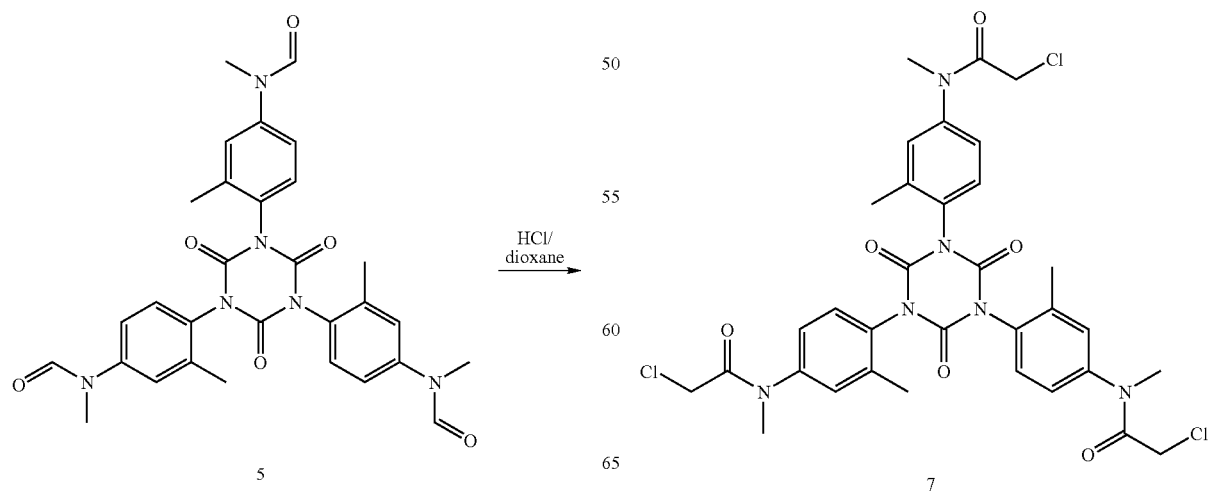

4 g) Preparation of 1,3,5-Tris-(N-chloroacetyl-N-methyl-4-amino-2-methyl-phenyl)-[1,3,5]triazinane-2,4,6-trione (7)

In a 100 ml round-bottom flask 6 (4.6 g, 9.5 mmol) was dissolved in DMA (15 ml) and chloroacetyl chloride (2.6 ml, 33 mmol) was added under stirring at 0° C. The reaction was stirred under argon at RT for 30 min or until HPLC showed complete chloroacetylation. The slurry was then poured into a large beaker with water (500 ml) under vigorous mechanical stirring. The precipitate formed was filtered off and dried in vacuo at 0.3 mbar (6.3 g). The pale solid was dissolved in 70 ml acetonitrile and poured into 500 ml H$_2$O under vigorous mechanical stirring. The precipitate formed was filtered off and left to dry in a desiccator (6.1 g, 89%).

4 h) Preparation of 1,3,5-Tris-(N-(DO3A t-butylester-acetamido)-N-methyl-4-amino-2-methyl-phenyl)-[1,3,5]triazinane-2,4,6-trione (8)

In a 50 ml round-bottom flask, 7 (0.50 g, 0.70 mmol) was suspended together with DO3A t-butyl ester (2.5 g, 4.2 mmol), diisopropylethylamine (910 μl, 5.2 mmol) and acetonitrile (15 ml). After sonication the reaction mixture was stirred at 75° C. under argon until LC/MS showed complete coupling. The solvents were then removed on rotary evaporator and the crude product (2.9 g) was used in the subsequent reaction.

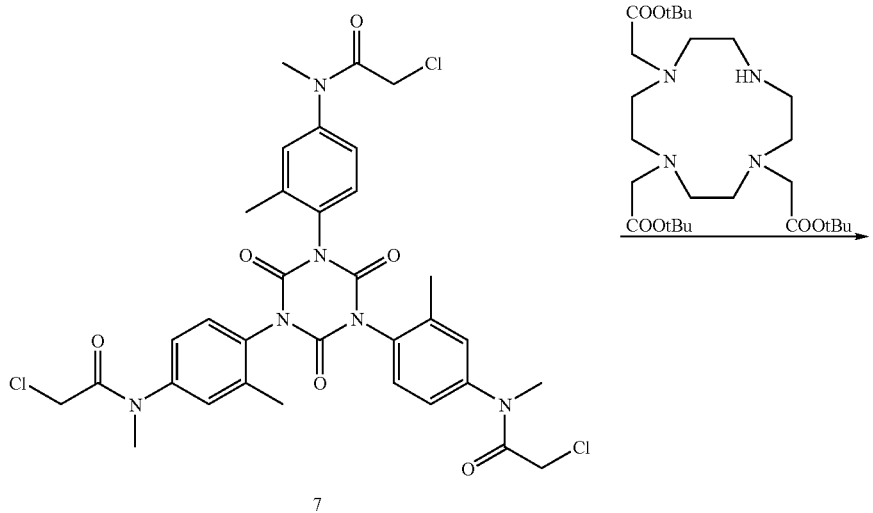

7

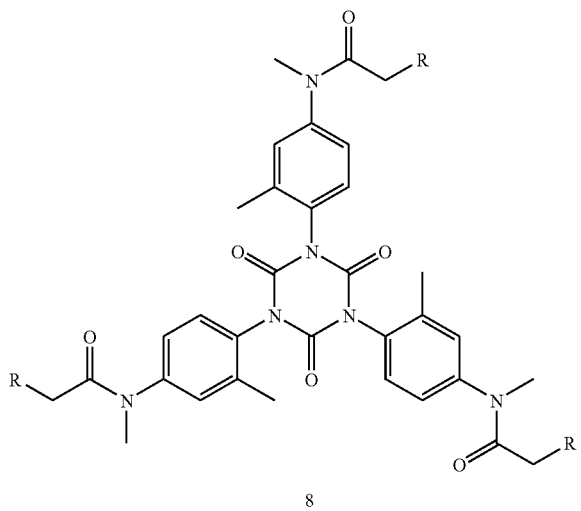

8

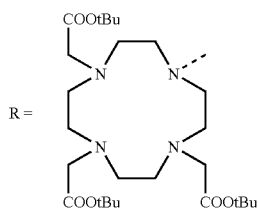

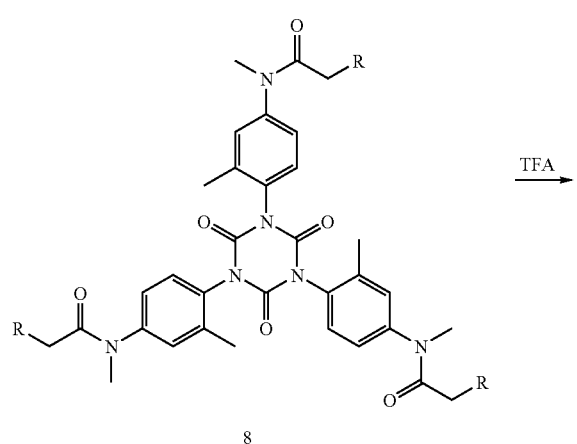

8

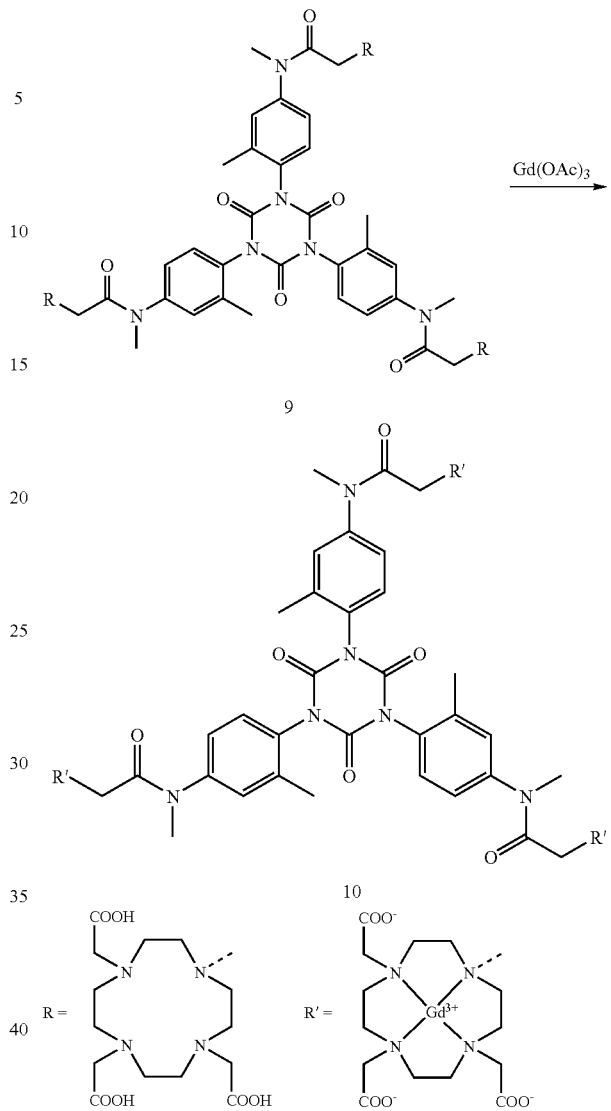

9

10

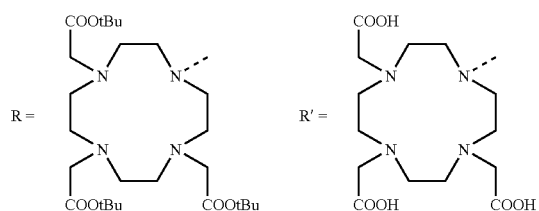

4i) Preparation of 1,3,5-Tris-(N-(DO3A-acetamido)-N-methyl-4-amino-2-methyl-phenyl)-[1,3,5]triazinane-2,4,6-trione (9)

The crude product of 8 (1.9 g) was dissolved in TFA (130 ml) and CH$_2$Cl$_2$ (130 ml) and was stirred at 50° C. under argon. The solution was stirred for 1 h or until LC/MS showed complete deprotection. The solvents were then removed on rotary evaporator and the residue was dried in vacuo overnight. The crude product (2.4 g) was then used in the final step.

4j) Preparation of gadolinium chelate of 1,3,5-Tris-(N-(DO3A-acetamido)-N-methyl-4-amino-2-methyl-phenyl)-[1,3,5]triazinane-2,4,6-trione (10)

The crude product of 9 (2.4 g) was dissolved in water and Gd(OAc)$_3$ (1.4 g, 4.2 mmol) was added under stirring. Vacuum (0.3 mbar) was then put on and the reaction was monitored continuously by LC/MS. When complete complexation was detected, the solvents were removed in vacuo. The crude product of 3.1 g was then purified by preparative HPLC (410 mg, 42% from 7)

Example 5

Synthesis of the trityl radical Tris-(8-carboxy-2,2,6,6-(tetra(methoxyethyl)benzo-[1,2-4,5']bis-(1,3)dithiole-4-yl)methyl sodium salt 10 g (70 mmol) Tris-(8-carboxy-2,2,6,6-(tetra(hydroxyethyl)benzo-[1,2-4,5']-bis-(1,3)-dithiole-4-yl)methyl sodium salt which had been synthesized according to Example 7 of WO-A1-98/39277 was suspended in 280 ml dimethylacetamide under an argon atmosphere. Sodium hydride (2.75 g) followed by methyl iodide (5.2 ml) was added and the reaction which is slightly exothermic was allowed to proceed for 1 hour in a 34° C. water bath for 60 min. The addition of sodium hydride and methyl iodide was repeated twice with the same amounts of each of the compounds and after the final addition, the mixture was stirred at room temperature for 68 hours and then poured into 500 ml water. The pH was adjusted to pH>13 using 40 ml of 1 M NaOH (aq) and the mixture was stirred at ambient temperature for 15 hours to hydrolyse the formed methyl esters. The mixture was then acidified using 50 ml 2 M HCl (aq) to a pH of about 2 and 3 times extracted the ethyl acetate (500 ml and 2×200 ml). The combined organic phase was dried over $Na_2SO_4$ and then evaporated to dryness. The crude product (24 g) was purified by preparative HPLC using acetonitrile/water as eluents. The collected fractions were evaporated to remove acetonitrile. The remaining water phase was extracted with ethyl acetate and the organic phase was dried over $Na_2SO_4$ and then evaporated to dryness. Water (200 ml) was added to the residue and the pH was carefully adjusted with 0.1 M NaOH (aq) to 7, the residue slowly dissolving during this process. After neutralization, the aqueous solution was freeze dried.

Example 6

Dynamic Nuclear Polarisation of a Composition Containing $^{13}C_1$-Pyruvic Acid, a Trityl Radical, a Gd-Chelate and Water Comparison Example 43 mg of a composition being 18.9 mM in trityl radical was prepared by dissolving the trityl radical of Example 5 in $^{13}C_1$-pyruvic acid. The Gd-chelate of Example 4 was added to result in a composition being 0.63 mM in Gd-chelate of Example 4, i.e. 1.89 mM in $Gd^{3+}$. The composition was mixed to homogeneity, placed in a probe cup and inserted in the DNP polariser. The composition was polarised under DNP conditions at 1.2 K in a 3.35 T magnetic field under irradiation with microwave (93.950 GHz). After 2 hours the polarisation was stopped and the composition was dissolved using a dissolution device according to WO-A-02/37132 in an aqueous solution of sodium hydroxide and TRIS to provide a neutral solution of hyperpolarised sodium $^{13}C_1$-pyruvate with a total pyruvate concentration of approximately 78 mM in 40 mM TRIS buffer.

Liquid state polarisation was determined by liquid state $^{13}C$-NMR at 400 MHz to be 44.7%.

Example 7

Dynamic Nuclear Polarisation of a Composition Containing TRIS-$^{13}C_1$-Pyruvate, a Trityl Radical, a Gd-Chelate and Water 11.7 mg 10 mM solution of the Gd-chelate of Example 4 was diluted with water to 40.1 mg total weight. To this solution were added 79.0 mg (0.65 mmol) TRIS and 57.6 mg $^{13}C_1$-pyruvic acid (90% purity, 0.65 mmol). The mixture was agitated until a clear solution of 160 µl volume was obtained. 3.47 mg of the trityl radical of Example 1 was dissolved in the solution result in a composition being 15 mM in trityl radical. The composition contained 29% (w/w) of pyruvate and was 0.7 mM in Gd-chelate of Example 4, i.e. 2.1 mM in $Gd^{3+}$. An aliquot of 137.4 mg of the composition was placed in a probe cup and inserted in a DNP polariser. The composition was polarised under DNP conditions at 1.2 K in a 3.35 T magnetic field under microwave irradiation (93.950 GHz). After 2.5 hours, the polarisation was stopped and the solid composition was dissolved in water containing 100 mg EDTA per liter.

Liquid state polarisation was determined by liquid state $^{13}C$-NMR at 400 MHz to be 36.9%. A liquid state polarisation of 36.9% was obtained. Hence by polarising TRIS-pyruvate rather than pyruvic acid, the nuclear spin polarisation of the $^{13}C$ nuclei present in the composition could be enhanced by the DNP polarisation to about ⅘ of the polarisation obtained in pyruvic acid. However, a broader range of Gd-chelates and trityl radicals can be used in the composition to polarise as the highly acidic conditions in pure pyruvic acid can be avoided and also reaction of pyruvic acid with Gd-chelates and/or the trityl radical to form unwanted by-products in the composition is no longer an issue.

Example 8

Dynamic Nuclear Polarisation of a Composition Containing TRIS-$^{13}C_1$-$D_2$-Fumarate, a Trityl Radical and Water A composition being 10 mM in trityl radical was prepared by dissolving the trityl radical tris-(8-carboxy-2,2,6,6-tetra(hydroxyethoxy)methylbenzo[1,2-d:4,5-d']-bis-(1,3-dithiol-4-yl)methyl sodium salt which was synthesized according to Example 29 in WO-A-97/09633 in a mixture of 0.21 mmol $^{13}C_1$-$D_2$-fumaric acid and 0.24 mmol TRIS dissolved in 17 µl water. The composition was mixed to homogeneity by a combination of vortex, light heating and ultrasound, placed in a probe cup and inserted in the DNP polariser. The composition was polarised under DNP conditions at 1.2 K in a 3.35 T magnetic field under irradiation with microwave (93.890 GHz). After 3 hours the polarisation was stopped.

The solid state polarisation was determined by solid state $^{13}C$-NMR carried out as described in Example 1 to be 220 (integral/mmol-13C).

Example 9

Dynamic Nuclear Polarisation of a Composition Containing TRIS-$^{13}C_1$-$D_2$-Fumarate, a Trityl Radical, a Gd-Chelate and Water In another experiment, a composition being 10 mM in trityl radical was prepared by dissolving the trityl radical tris-(8-carboxy-2,2,6,6-tetra(hydroxyethoxy)-methylbenzo[1,2-d:4,5-d']-bis-(1,3-dithiol-4-yl)methyl sodium salt which was synthesized according to Example 29 in WO-A-97/09633 in a mixture of 0.21 mmol $^{13}C_1$-$D_2$-fumaric acid and 0.24 mmol TRIS dissolved in 17 µl water. Further, the Gd-chelate of Example 4 was added to result in a composition being 0.7 mM in the Gd-chelate, i.e. 2.1 mM in $Gd^{3+}$. The composition was mixed to homogeneity, by a combination of vortex, light heating and ultrasound, and placed in a probe cup and inserted in the DNP polariser. The composition was polarised under DNP conditions at 1.2 K in a 3.35 T magnetic field under irradiation with microwave (93.890 GHz). After 3 hours the polarisation was stopped.

The solid state polarisation was determined by solid state $^{13}C$-NMR as described in Example 1b to be 630 (integral/mmol-13C).

Example 10a

Production of a Solution of Hyperpolarised TRIS-$^{13}C_1$-Fumarate

The polarised solid composition of Example 8 was dissolved using a dissolution device according to WO-A-02/37132 in an aqueous solution of sodium hydroxide to provide a neutral solution of hyperpolarised TRIS-$^{13}C_1$-fumarate with a total fumarate concentration of about 40 mM in 40 mM TRIS buffer.

Liquid state polarisation was determined by liquid state $^{13}C$-NMR at 400 MHz to be 9%.

Example 10b

Production of a Solution of Hyperpolarised TRIS-$^{13}C_1$-Fumarate

The polarised solid composition of Example 9 was dissolved using a dissolution device according to WO-A-02/37132 in an aqueous solution of sodium hydroxide to provide a neutral solution of hyperpolarised TRIS-$^{13}C_1$-fumarate with a total fumarate concentration of about 40 mM in 40 mM TRIS buffer.

Liquid state polarisation was determined by liquid state $^{13}C$-NMR at 400 MHz to be 23%.

Example 11

Dynamic Nuclear Polarisation of a Composition Containing TRIS-$^{13}C_1$-Acetate, a Trityl Radical and Water A composition being 10 mM in trityl radical was prepared by dissolving the trityl radical tris-(8-carboxy-2,2,6,6-tetra(hydroxyethoxy)methylbenzo[1,2-d:4,5-d']-bis-(1,3-dithiol-4-yl)methyl sodium salt which was synthesized according to Example 29 in WO-A-97/09633 in a mixture of 0.199 mmol TRIS-$^{13}C_1$-acetate and 13 μl water. The composition was mixed to homogeneity by a combination of vortex, light heating and sonication, placed in a probe cup and inserted in the DNP polariser. The composition was polarised under DNP conditions at 1.2 K in a 3.35 T magnetic field under irradiation with microwave (93.890 GHz). After 3 hours the polarisation was stopped.

The solid state polarisation was determined by solid state $^{13}C$-NMR carried out as described in Example 1 to be 195 (integral/mmol-13C).

Example 12

Dynamic Nuclear Polarisation of a Composition Containing TRIS-$^{13}C_1$-Acetate, a Trityl Radical, a Gd-Chelate and Water A composition being 10 mM in trityl radical was prepared by dissolving the trityl radical tris-(8-carboxy-2,2,6,6-tetra(hydroxyethoxy)-methylbenzo[1,2-d:4,5-d']-bis-(1,3-dithiol-4-yl)methyl sodium salt which was synthesized according to Example 29 in WO-A-97/09633 in a mixture of 0.199 mmol TRIS-$^{13}C_1$-acetate and 13 μl water. Further, the Gd-chelate of Example 4 was added to result in a composition being 0.2 mM in the Gd-chelate, i.e. 0.6 mM in $Gd^{3+}$. The composition was mixed to homogeneity, by a combination of vortex, light heating and sonication, placed in a probe cup and inserted in the DNP polariser. The composition was polarised under DNP conditions at 1.2 K in a 3.35 T magnetic field under irradiation with microwave (93.890 GHz). After 3 hours the polarisation was stopped.

The solid state polarisation was determined by solid state $^{13}C$-NMR as described in Example 1 to be 450 (integral/mmol-13C).

Example 13

Dynamic Nuclear Polarisation of a Composition Containing TRIS-$^{13}C_1$-Glutamate, a Trityl Radical, a Gd-Chelate and Water A composition being 16 mM in trityl radical was prepared by dissolving the trityl radical tris-(8-carboxy-2,2,6,6-tetra(hydroxyethoxy)-methylbenzo[1,2-d:4,5-d']-bis-(1,3-dithiol-4-yl)methyl sodium salt which was synthesized according to Example 29 in WO-A-97/09633 in a mixture of 0.06 mmol $^{13}C_1$-glutamic acid, 74 μmol TRIS and 7 μl water. Further, the Gd-chelate of Example 4 was added to result in a composition being 0.3 mM in the Gd-chelate, i.e. 0.9 mM in $Gd^{3+}$. The composition was mixed to homogeneity by a combination of vortex, light heating and sonication, placed in a probe cup and inserted in the DNP polariser. The composition was polarised under DNP conditions at 1.2 K in a 3.35 T magnetic field under irradiation with microwave (93.890 GHz). After 3 hours the polarisation was stopped and the composition was dissolved using a dissolution device according to WO-A-02/37132 in an aqueous solution to provide a neutral solution of hyperpolarised TRIS-$^{13}C$-glutamate with a total concentration of approximately 10 mM.

Liquid state polarisation was determined by liquid state $^{13}C$-NMR at 400 MHz to be 25%.

Example 14

Dynamic Nuclear Polarisation of a Composition Containing TRIS-$^{13}C_1$-Aspartate, a Trityl Radical, a Gd-Chelate and Water A composition being 16 mM in trityl radical was prepared by dissolving the trityl radical tris-(8-carboxy-2,2,6,6-tetra(hydroxyethoxy)-methylbenzo[1,2-d:4,5-d']-bis-(1,3-dithiol-4-yl)methyl sodium salt which was synthesized according to Example 29 in WO-A-97/09633 in a mixture of 0.058 mmol $^{13}C_1$-aspartic acid, 72 μmol TRIS and 7 μl water. Further, the Gd-chelate of Example 4 was added to result in a composition being 0.3 mM in the Gd-chelate, i.e. 0.9 mM in $Gd^{3+}$. The composition was mixed to homogeneity by a combination of vortex, light heating and sonication, placed in a probe cup and inserted in the DNP polariser. The composition was polarised under DNP conditions at 1.2 K in a 3.35 T magnetic field under irradiation with microwave (93.890 GHz). After 3 hours the polarisation was stopped and the composition was dissolved using a dissolution device according to WO-A-02/37132 in an aqueous solution to provide a neutral solution of hyperpolarised TRIS-$^{13}C_1$-aspartate with a total concentration of approximately 10 mM.

Liquid state polarisation was determined by liquid state $^{13}C$-NMR at 400 MHz to be 16%.

What is claimed is:

1. A composition comprising a hyperpolarised carboxylate salt formed by an organic carboxylic acid and an organic amine or amino compound, a DNP agent and optionally a paramagnetic metal ion, wherein the carboxylate of the organic acid is endogenous and $^{13}C$ enriched, the organic amine or amino compound is physiologically tolerable aminoalcohol with a molecular weight of 30 to 300 g/mol; and the hyperpolarized carboxylate salt is obtained by subjecting the carboxylate salt to dynamic nuclear polarization in the presence of a DNP agent and optionally a paramagnetic metal ion.

2. The composition according to claim 1 wherein the composition is a liquid composition, preferably a composition dissolved in a solvent or solvent mixture.

3. The composition according to claim 1 wherein the carboxylate plays a role in a metabolic process in the human or non-human animal body.

4. The composition according to claim 1 wherein the carboxylate is enriched at a carboxyl-C-atom, a carbonyl-C-atom or a quaternary C-atom.

5. The composition according to claim 1 wherein the DNP agent is a stable oxygen-based, sulphur-based or carbon-based trityl radical.

6. The composition according to claim 1 wherein the trityl radical is a radical of the formula (1)

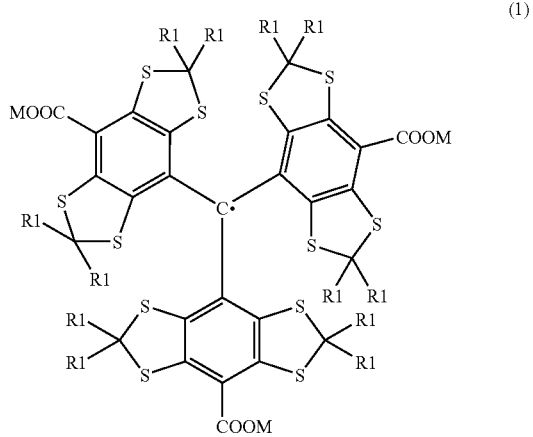

(1)

wherein
M represents hydrogen or one equivalent of a cation; and
R1 which is the same or different represents a straight chain or branched $C_1$-$C_6$-alkyl group, $C_1$-$C_6$-hydroxyalkyl group or a group —$(CH_2)_n$—X—R2, wherein n is 1, 2 or 3;
X is O or S and R2 is a straight chain or branched $C_1$-$C_4$-alkyl group.

7. The composition according to claim 1 wherein the composition comprises a paramagnetic metal ion, preferably a paramagnetic metal ion of a lanthanide metal of atomic numbers 58-70 or of a transition metal of atomic numbers 21-29, 42 or 44.

8. The composition according to claim 7 wherein the paramagnetic metal ion is soluble in the carboxylate, preferably in the carboxylate dissolved in a solvent or a solvent mixture.

9. A method for producing a solid hyperpolarised carboxylate salt of an organic carboxylic acid and an organic amine or amino compound, wherein the carboxylate is an endogenous carboxylate being $^{13}C$ enriched, and the organic amine or amino compound is a physiologically tolerable aminoalcohol with a molecular weight of 30 to 300 g/mol, the method comprising preparing a composition comprising the carboxylate salt, a DNP agent, preferably a trityl radical and optionally a paramagnetic metal ion and carrying out dynamic nuclear polarisation on the composition.

10. A method for producing a liquid hyperpolarised carboxylate salt of an organic carboxylic acid and an organic amine or amino compound, wherein the carboxylate is an endogenous carboxylate being $^{13}C$ enriched, and the organic amine or amino compound is a physiologically tolerable aminoalcohol with a molecular weight of 30 to 300 g/mol, the method comprising preparing a composition comprising the carboxylate salt, a DNP agent, preferably a trityl radical and optionally a paramagnetic metal ion, carrying out dynamic nuclear polarisation on the composition and liquefying the composition, by dissolution.

11. The composition according to claim 1, wherein the carboxylate salt formed by an organic carboxylic acid and an organic amine or amino compound is selected from the group of TRIS-$^{13}C_1$-pyruvate, TRIS-$^{13}C_1$-$D_2$-fumarate, TRIS-$^{13}C_1$-fumarate, TRIS-$^{13}C_1$-acetate, TRIS-$^{13}C_1$-glutamate, TRIS-$^{13}C_1$-aspartate.

12. The composition of claim 1 that is devoid of any glass formers.

13. The method of claim 9 wherein the composition is devoid of any glass formers.

14. The method of claim 10 wherein the composition is devoid of any glass formers.

15. A solid composition comprising a hyperpolarised carboxylate salt formed by an organic carboxylic acid and an organic amine or amino compound, a DNP agent and optionally a paramagnetic metal ion, wherein the carboxylate of the organic acid is endogenous and $^{13}C$ enriched, the organic amine or amino compound is physiologically tolerable aminoalcohol with a molecular weight of 30 to 300 g/mol.

16. The solid composition of claim 15 that the is physiologically tolerable aminoalcohol is selected from tris(hydroxymethyl)methylamine (TRIS) and N-methyl- D-glucamine (meglumine), preferably is tris(hydroxymethyl) methylamine (TRIS).

17. The solid composition of claim 15 that said endogenous carboxylate is selected from malate, acetate, fumarate, lactate, citrate, pyruvate, bicarbonate, malonate, succinate, oxaloacetate, [alpha]-ketoglutarate, glutamate, aspartate, and isocitrate, preferably from acetate, fumarate, glutamate, aspartate and pyruvate.

18. The solid composition of claim 15 comprising said paramagnetic metal ion, wherein the paramagnetic metal ions are in chelated form.

19. A hyperpolarised carboxylate salt by first forming a carboxylate salt by an organic carboxylic acid and an organic amine or amino compound followed by carrying out dynamic nuclear polarisation on said carboxylate salt, wherein the carboxylate of the organic acid is endogenous and $^{13}C$ enriched, and the organic amine or amino compound is a physiologically tolerable aminoalcohol with a molecular weight of 30 to 300 g/mol.

* * * * *